US006265147B1

(12) United States Patent
Mobley et al.

(10) Patent No.: US 6,265,147 B1
(45) Date of Patent: Jul. 24, 2001

(54) METHOD OF SCREENING FOR NEUROPROTECTIVE AGENTS

(75) Inventors: William C. Mobley, Palo Alto; Ronald J. Weigel, Woodside; Chengbiao Wu, San Jose; Har Hiu Dawn Lam, Stanford, all of CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/452,531

(22) Filed: Dec. 1, 1999

(51) Int. Cl.$^7$ ........................................................ C12Q 1/00
(52) U.S. Cl. ................................ 435/4; 435/69.1; 514/169
(58) Field of Search ........................ 435/4, 69.1; 514/12, 514/169, 182

(56) References Cited

U.S. PATENT DOCUMENTS 5,135,956 * 8/1992 Borg et al. ............................ 514/724
5,554,601 * 9/1996 Simplins et al. ...................... 514/182
5,723,291 * 3/1998 Kushner et al. ......................... 435/6
5,843,934 * 12/1998 Simpkins .............................. 514/182

OTHER PUBLICATIONS

Carmeci C. Identification of a Gene (GPR30) . . . Genomics 45:607–617, 1997.*
Hermann C. Quantitative Analysis of the Complex Between p21 and the Ras–Binding Domain of the Human Raf–1 Protein Kinase. J Biol Chem 270(7)2901–2905, Feb. 1995.*
Carmeci, Charles, et al., "Identification of a Gene (GPR30) with Homology to the G–Protein–Coupled Receptor Superfamily Associated with Estrogen Receptor Expression in Breast Cancer," *Genomics* (1997) vol. 45:607–617.
Owman, Christer, et al., "Cloning of Human cDNA Encoding a Novel Hepathelix Receptor Expressed in Burkitt's Lymphoma and Widely Distributed in Brain abd Peripheral Tissues," *Biochemical and Biophysical Research Cimmunications* (1996) vol. 228:285–292.
Singh, Meharvan, et al., "Estrogen–Induced Activation of Mitogen–Activated Protein Kinase in Cerebral Cortical Explants: Convergence of Estrogen and Neurotrophin Signaling Pathways," *Journal of Neuroscience* (Feb. 15, 1999) vol. 19(4):1179–1188.
Toran–Allerand, C. Dominique, "The Estrogen/Neurotrophin Connection During Neural Development: Is Co–Localization of Estrogen Receptors with the Neurotrophins and Their Receptors Biologically Revelant?", *Dev. Neurosci.* (1996) vol. 18:36–48.
Genbank Accession Number Y08162.

* cited by examiner

*Primary Examiner*—Ralph Gitomer
(74) *Attorney, Agent, or Firm*—Pamela Sherwood; Bozicevic, Field & Francis LLP (57) ABSTRACT

Neurological dysfunction is prevented or treated by the administration of ligands that activate the GPR30 receptor. Ligands include, but are not limited to, estrogens and structurally related molecules. In a preferred embodiment, the GPR30 ligand is an orally available drug that can cross into the brain from blood. Of particular interest are ligands that do not activate other estrogen receptors, and therefore do not have the classical estrogenic effects attributable to these receptors.

4 Claims, 5 Drawing Sheets

METHOD OF SCREENING FOR NEUROPROTECTIVE AGENTS

Neurodegenerative diseases are characterized by the dysfunction and death of neurons, leading to the loss of neurologic functions mediated by the brain, spinal cord and the peripheral nervous system. These disorders have a major impact on society. For example, approximately 4 to 5 million Americans are afflicted with the chronic neurodegenerative disease known as Alzheimer's disease. Other examples of chronic neurodegenerative diseases include diabetic peripheral neuropathy, multiple sclerosis, amyotrophic lateral sclerosis, Huntington's disease and Parkinson's disease. Normal brain aging is also associated with loss of normal neuronal function and may entail the depletion of certain neurons. Not all neurodegenerative diseases are chronic. Stroke is an acute neurodegenerative disease. Sudden loss of neurons may also characterize the brains of patients with epilepsy and those that suffer hypoglycemic insults and traumatic injury of the brain, peripheral nerves or spinal cord.

Though the mechanisms responsible for the dysfunction and death of neurons in neurodegenerative disorders are not well understood, a common theme is that loss of neurons results in both the loss of normal functions and the onset of adverse behavioral symptoms. For example, patients with Alzheimer's disease demonstrate memory loss and cognitive deficits as well as bizarre and sometimes aggressive behaviors. Therapeutic agents that have been developed to retard loss of neuronal activity and survival are largely ineffective. Some have toxic side effects that limit their usefulness. Other promising therapies, such as neurotrophic factors, are prevented from reaching their target site because of their inability to cross the blood-brain barrier. The blood-brain barrier is a complex of structural and enzymatic components that retards the passage of both large and charged small molecules, thereby limiting the access of such molecules to cells in the brain.

Senile dementia of the Alzheimer's type is a debilitating neurodegenerative disease, mainly afflicting the elderly; it is characterized by a progressive intellectual and personality decline, as well as a loss of memory, perception, reasoning, orientation and judgment. One highly reproducible feature of the disease is dysfunction and loss of selected populations of neurons in the brain. Among these are cholinergic neurons of the basal forebrain, whose normal function contributes importantly to attention, learning and memory. There is an observed decline in the function of cholinergic systems, and a severe depletion of these cholinergic neurons.

It is increasingly apparent that estrogen has an important role in regulating neuronal survival and function. There is perhaps no better demonstration of this than the finding that administration of estrogen to postmenopausal women significantly decreases the incidence of Alzheimer's disease. These striking data have encouraged new interest in the biological functions of estrogen and, in particular, of its actions on neurons.

In recent years it has become apparent that estrogen enhances the differentiation of neurons, including the outgrowth of processes from CNS neurons; estrogen binds to specific receptors on neurons in the brain and regulates the levels of classical neurotrophic factors, including nerve growth factor (NGF) and brain-derived neurotrophic factor (BNDF), and their receptors. These findings are evidence that estrogen is itself a neurotrophic factor, and they argue strongly that estrogen's neurotrophic actions are responsible for enhancing the survival and function of neurons important for memory and learning in postmenopausal women. Indeed, these data have suggested that estrogen's neurotrophic actions could benefit the function and survival of neurons in both women and men and that estrogen, or an estrogen derivative that is active on estrogen receptors, could be used to treat patients with disorders in which there is dysfunction and death of neurons.

Estrogen elicits a selective enhancement of the growth and differentiation of axons and dendrites (neurites) in the developing brain. Widespread colocalization of the receptors for estrogen and neurotrophic factors in a number of neuronal populations, including neurons of the basal forebrain, cerebral cortex, sensory ganglia, and PC12 cells, has been correlated with the differential and reciprocal transcriptional regulation of these receptors by their ligands. Even more important, estrogen and neurotrophic factor receptor coexpression leads to convergence or cross-coupling of their signaling pathways, particularly at the level of the mitogen-activated protein (MAP) kinase cascade. The ability of estrogen to regulate a broad array of cytoskeletal and growth-associated genes involved in neurite growth and differentiation is of great interest in the development of pharmaceutical agents and methodologies for the treatment of neurological disorders.

Relevant Literature

Estrogen elicits a selective enhancement of the growth and differentiation of axons and dendrites (neurites) in the developing CNS. There is widespread colocalization of estrogen and neurotrophin receptors within developing forebrain neurons and reciprocal transcriptional regulation of these receptors by their ligands (Toran-Allerand (1996) *Dev Neurosci* 18(1–2):36–48). Estradiol elicited rapid tyrosine phosphorylation/activation of mitogen-activated protein (MAP) kinases. This extracellular signal-regulated protein kinase activation was inhibited successfully by the MEK1 inhibitor PD98059, but not by the estrogen receptor (ER) antagonist ICI 182,780, and did not appear to result from estradiol-induced activation of trk (Singh et al. (1999) *J Neurosci* 19(4):1179–88).

U.S. Pat. No. 5,843,934, issued Dec. 1, 1998, a method is described for conferring a cytoprotective effect on a population of cells by administering an estrogen compound having insubstantial sex related activity.

SUMMARY OF THE INVENTION

Compositions and methods are provided for the treatment of neurological dysfunction, by the administration of ligands that activate the GPR30 receptor. Ligands include, but are not limited to, estrogens and structurally related molecules. Conditions that benefit from protection of neurons include brain trauma, stroke, multiple sclerosis, neurodevelopmental disorders and neurodegenerative disorders including, but not limited to, Alzheimer's disease, Parkinson's disease, and amyotrophic lateral sclerosis.

In a preferred embodiment, the GPR30 ligand is an orally available drug that can cross into the brain from blood. Of particular interest are estrogen derivatives that do not activate other estrogen receptors, and therefore do not have the classical estrogenic effects attributable to these receptors.

DETAILED DESCRIPTION OF THE INVENTION

Neurological disorders are treated by administering a therapeutic dose of a ligand to the GPR30 receptor. The GPR30 receptor is expressed in neural cells, and when activated can provide for neuroprotection from trauma and disease. While GPR30 can be activated by estrogens, it is distinct from the classical estrogen receptors. Of particular interest are estrogen derivatives that do not activate other estrogen receptors, and therefore do not have the classical estrogenic effects attributable to these receptors. In a preferred embodiment, the GPR30 ligand is an orally available drug that can cross into the brain from blood.

The subject methods are used for prophylactic or therapeutic purposes. As used herein, the term "treating" is used to refer to both prevention of disease, and treatment of pre-existing conditions. The prevention of disease is accomplished by administration of the GPR30 ligands prior to development of overt disease. The treatment of ongoing disease, in order to stabilize or improve the clinical symptoms of the patient, is of particular interest. Such treatment is desirably performed prior to complete loss of function in the affected tissues.

The GPR30 receptor is also used in screening assays to determine ligands that are suitable for use in the neuroprotective methods. Test compounds are screened for those that have the desired properties, through their specific binding and activation of GPR30, which preferably lack estrogen action at classical estrogen response elements. Compounds of interest for screening include, without limitation, combinatorial libraries of steroid and steroid derivatives; targeted modifications of estrogenic compounds; environmental compounds, which can be derived from a wide variety of sources including plants, soil, water, foods; synthetic compounds such as chlorinated organics, polycyclic aromatic hydrocarbons, herbicides; pesticides; pharmaceuticals; and the like.

Definitions

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention which will be limited only by the appended claims.

"Neurologic disorder" is defined here and in the claims as a disorder in which dysfunction and loss of neurons occurs either in the peripheral nervous system or in the central nervous system. Examples of neurodegenerative disorders include: chronic neurodegenerative diseases such as Alzheimer's disease, Parkinson's disease, Huntington's chorea, diabetic peripheral neuropathy, multiple sclerosis, amyotrophic lateral sclerosis; aging; and acute neurodegenerative disorders including: stroke, traumatic brain injury, peripheral nerve damage, hypoglycemia, spinal cord injury, epilepsy, and anoxia and hypoxia.

GPR30: The G protein coupled receptor, GPR30 is described in the art, for example see Owman et al. (1996) *Biochem. Biophys. Res. Commun.* 228:285–292; or Carmeci et al. (1997) *Genomics* 45:607–617. GPR30 was discovered as a result of its increased expression in ER-positive breast carcinoma cell lines, but not in ER-negative breast carcinoma cell lines. Overexpression of GRP30 confers increased estrogen responsivity to cells derived from breast cancer tissue. GPR30 is expressed in the brain (Carmeci et al. (1997) *Genomics* 45:607–617). It is structurally distinct from all other known estrogen receptors.

The nucleotide sequence of naturally occurring human GPR30 may be accessed in Genbank, accession number Y08162. Those of skill in the art can easily use the nucleotide sequences to produce the coding sequence, to genetically modify cells to express the protein, or to produce the purified GPR30 polypeptide for screening and other assays.

The nucleic acids of the invention can be introduced into suitable host cells using a variety of techniques which are available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like. The nucleic acids can be provided as a linear molecule or within a circular molecule. They can be provided within autonomously replicating molecules (vectors) or within molecules without replication sequences. They can be regulated by their own or by other regulatory sequences, as is known in the art.

The nucleic acid encoding GPR30 are used to express a partial or complete gene product. Constructs can be generated by recombinant methods, synthetically, or in a singlestep assembly of a gene and entire plasmid from large numbers of oligodeoxyribonucleotides is described by, e.g. Stemmer et al., *Gene* (Amsterdam) (1995) 164(1):49–53. The choice of appropriate vector is well within the skill of the art. Many such vectors are available commercially.

Appropriate nucleic acid constructs are purified using standard recombinant DNA techniques as described in, for example, Sambrook et al., Molecular Cloning: A Laboratory Manual, 2nd Ed., (1989) Cold Spring Harbor Press, Cold Spring Harbor, N.Y. The gene product encoded by a nucleic acid of the invention is expressed in any expression system, including mammalian cells, and particularly human neural cells.

The coding sequences may be linked to regulatory sequences as appropriate to obtain the desired expression properties. These can include promoters attached either at the 5' end of the sense strand or at the 3' end of the antisense strand, enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used.

GPR30 Ligands: Ligands to the GPR30 are molecules that specifically bind to the GPR30 receptor. Such ligands can include low molecular weight native molecules, such as estrogens, as well as synthetic derivative compounds such as diethylstilbesterol. Ligands of particular interest are able to bind to GPR30 protein to create a ligand/receptor complex. GPR30 is a G-protein coupled receptor whose overall structure is distinct from that of all other known estrogen receptors and, indeed form the structural class into which these other receptors fall. While some of the ligands for GPR30 are shared with these other receptors, others are expected to be distinct, binding only to GPR30. A compound that binds a steroid receptor and mimics the effects of the native ligand may be referred to as an "agonist", while a compound that inhibits this effect is called an "antagonist."

The effectiveness of known modulators of steroid receptors is often tempered by their undesired side-effect profile, particularly during long-term administration. For example, the effectiveness of diethylstilbesterol respectively, as female birth control agents must be weighed against the increased risk of breast cancer and heart disease to women taking such agents. Accordingly, GPR30 ligands of interest have good specificity for binding GPR30 receptors, but which have reduced or no cross-reactivity for other steroid or intracellular receptors.

Estrogens: is a generic term used to refer to a class of steroid or non-steroid estrogenic hormones. Various substances including not only natural substances, but also synthetic substances, are known as estrogens (Environmental Health Perceptives (1985) Vol. 61, pp. 97–110). Various assays may be used to determine whether a compound has estrogenic activity, for example, cellular assays as described in Webb et al. (1993) *Mol. Endocrinol.* 6:157–167.

Frequently the term estrogen is used to refer to the three naturally produced estrogens that are present in significant quantities in the plasma of human females: 17β-estradiol, estrone, and estriol. These compounds have the following chemical structures.

In mammalian cells, the estrogens 17β-estradiol and estrone are continuously interconverted by 17β-oxidoreductase, and are generally metabolized via two major pathways: hydroxylation at the 16α-position or hydroxylation at the 2- or 4-position by cytochrome P-450. The latter pathway produces catechol estrogens.

Other estrogen compounds included in this definition are estrogen derivatives, estrogen metabolites and estrogen precursors as well as those molecules capable of binding cell associated estrogen receptor as well as other molecules where the result of binding specifically triggers a characterized estrogen effect. Also included are mixtures of more than 1 estrogen.

Of particular interest for the subject methods are estrogen derivatives, a great many of which have been described in the art. The extensive literature on steroid chemistry provides a wide variety of compounds for use in the subject screening and therapeutic methods. To provide only a small example, some known derivatives of estrogens include alpha-estradiol dipropionate, estradiol mustard, polyestradiol phosphate, estradiol 3-[bis(2-chloroethyl)carbamate], estradiol cyclopentylpropionate, beta-estradiol diacetate, estradiol undecylate, 2-hydroxyestradiol, beta-estradiol-3-benzoate, cloxestradiol, 6 β-hydroxyestradiol-17β, 17-ethynyl estradiol, estradiol, 4-hydroxyestradiol, ethynylestradiol 3-methyl ether, estradiol-17-valerate, estradiol-17-caprylate, estradiol-17α 3-d-glucuronoside, 17α-(n-acetyl-d-glucosaminyl)-estradiol 3-d-glucuronoside, 2-methoxyestradiol-17β, estradiol 17-octadecanoate, almestrone, neo-oestronol ii, nitroestrone, estrone benzoate, 2-hydroxyestrone, sodium estrone sulfate, estrone-3-sulfate, stilbestrone, neo-estrone, quingestrone, anhydrohydroxynorprogestrone, pentagestrone, metigestrona, piperazine estrone sulfate, fluoxymestrone, westron, edogestrone, 16α-hydroxyestrone, 2-methoxyestrone, estrone-2,4,16,16-d4, estrone-16,16-d2, estrone-2,4-d2, estriol propionate, estriol acetate benzoate, nilestriol, estriol succinate, epiestriol, 3-methoxy-17-epiestriol; and the like as known in the art.

Estrogen receptor: as used herein, is intended to mean the "classical" estrogen receptors. The molecules are also known as ESR1 (estrogen receptor α) and ESR2 (estrogen receptor β). The sequences of these proteins and corresponding nucleic acids are well known in the art. ESR1 is a member of the superfamily of nuclear receptors, which can transduce extracellular signals into transcriptional responses. The nucleotide sequence encoding ESR1 was described by Green et al. (1986) *Nature* 320:134–139, 1986; and Green et al. (1986) *Science* 231:1150–1154. The sequences may be accessed at Genbank, accession number NM_000125.

ESR2 is homologous to ESR1 and has an overlapping but nonidentical tissue distribution. The DNA-binding domain of ESR-β is 96% conserved compared to ESR1, and the ligand-binding domain shows 58% conserved residues (Mosselman et al. (1996) *FEBS Lett.* 392:49–53). The sequence may be accessed at Genbank, accession number AF051427.

In preferred embodiments of the invention, the methods utilize GPR30 ligands that do not substantially activate ESR1 or ESR2. Therefore, in screening compounds, one may determine two attributes for a candidate compound: whether it activates GPR30, and whether it lacks activation of ESR1 and/or ESR2. Activation of ESR1 and ESR2 by hormone involves at least two steps. First, hormone binding initially relieves repression, a property imposed on ER in cis by its ligand-binding domain (EBD). Subsequently, the derepressed ER binds specific genomic sites and regulates transcription. In addition to the natural hormone, ER binds a broad range of ligands that evoke a spectrum of responses ranging from full ER activation by agonists to partial activation and inhibition by partial or complete antagonists.

A number of assays have been described in the literature for determining whether a candidate compound has activity on ERs. For example, Logie et al. (1998) *Mol Endocrinol* 12(8):1120–32 describe a nontranscriptional assay for responsiveness based on Flp recombinase/human EBD protein chimeras. These fusion proteins transduce the transient event of ligand binding into a permanent DNA change in a human cell line system. Agonists and antagonists can be functionally distinguished in a nontranscriptional assay. The ability of a cell line to activate a transfected estrogen response element (ERE)-containing reporter gene is assessed by Zhang et al. (1999) *Mol Endocrinol* 13(4):632–43. Competition binding analysis for estrogen receptors are well known, e.g. see Hanstein et al. (1999) *Mol Endocrinol* 13(1):129–37.

U.S. Pat. No. 5,723,291, Kushner et al. describes methods for screening compounds with activity at ERs. The assay use cells comprising promoters having an AP1 site linked to a reporter gene. Compounds capable of inducing or blocking expression of the reporter gene can thus be identified. Jorgensen et al. (1998) *APMIS* 106(1):245–51 reviews combinations of assay methods, such as direct in vitro measurement of interaction between a potential estrogenic chemical and the ER with methods that are based on mammalian cells or whole animals, or to assay gene expression directly by methods such as differential display, where the expression of both genes known to be regulated directly by the receptor and genes regulated by other pathways can be monitored.

Drug Screening Assays: These are used to identify GPR30 ligands that bind to and activate the GPR30 receptor. Drug screening identifies agents that enhance GPR30 activity. Of particular interest are screening assays for agents that have a low toxicity for human cells. In vitro or in vivo binding assays can be used to assess the extent to which a compound behaves as a specific ligand. Other assays are available to test for the activation of signaling pathways by ligand binding. One assay based on the finding that GPR30 activation results in the activation of the small GTPase Rap1, and of the other enzymes in the MAP kinase signaling pathway that is activated by Rap1. The assay for evaluating the activation of Rap1 examines the extent to which Rap1 is bound to GTP and employs a method as described by Herrmann et al. (1995) *J. Biol. Chem* 270:2901–2905. A wide variety of assays are available to assess the activation status of the enzymes downstream from Rap1. These include in vitro kinase assays for B-Raf, MEK, MAP kinase and Rsk (Cowley et al. (1994) *Cell* 77:841–852; Vossler et al. (1997) *Cell* 89:73–82). The activation of these proteins and some of their downstream targets (e.g. Elk-1 and CREB) may also be assessed through the use of antibodies to phosphorylated tyrosine or serine or threonine residues, which marks their active state (Payne et al. (1991) *EMBO J.* 10(4):885–892).

The GPR30 protein may also be used for determination of three-dimensional crystal structure, which can be used for modeling intermolecular interactions, including those that characterize the binding of a ligand to GPR30. One may examine the interactions of ligands with receptors, as reviewed by Borman (1992) *Chem. Eng. News* 70:18–26. Drug design may include studies which focus on the binding of a ligand to a protein, including assays for the detection of ligand binding.

The term "agent" as used herein describes any molecule, e.g. small organic molecule, with the capability of binding to, and activating GPR30. Generally a plurality of assay mixtures are run in parallel with different agent concentrations to obtain a differential response to the various concentrations. Typically, one of these concentrations serves as a negative control, ie. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups.

For example, candidate agents may utilize the structures and methods described by Fink et al. (1999) *Chem. Biol.* 6:205–219, of an estrogen pharmacophore that consists of a simple heterocyclic core scaffold, amenable to construction by combinatorial methods, onto which are appended 3–4 peripheral substituents that embody substructural motifs commonly found in nonsteroidal estrogens. Members of the imidazole, thiazole or isoxazole classes generally have weak binding for ESR1, and are well suited for combinatorial synthesis using solid-phase methods.

Candidate agents may be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Pharmaceutical Formulation: The GPR30 ligand may be combined with a pharmaceutically acceptable carrier, which term includes any and all solvents, dispersion media, coatings, anti-oxidant, isotonic and absorption delaying agents and the like. The use of such media and agents for pharmaceutically active substances is well known in the art. Except insofar as any conventional media or agent is incompatible with the active ingredient, its use in the therapeutic compositions and methods described herein is contemplated. Supplementary active ingredients can also be incorporated into the compositions.

The formulation may be prepared for use in various methods for administration. The formulation may be given orally, by inhalation, or may be injected, e.g. intravascular, intratumor, subcutaneous, intraperitoneal, intramuscular, etc.

The dosage of the therapeutic formulation will vary widely, depending upon the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc. to maintain an effective dosage level. In some cases, oral administration will require a higher dose than if administered intravenously.

The GPR30 ligand of the invention can be incorporated into a variety of formulations for therapeutic administration. More particularly, the complexes can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the GPR30 ligand can be achieved in various ways. The GPR30 ligand may be systemic after administration or may be localized by the use of an implant that acts to retain the active dose at the site of implantation.

The following methods and excipients are merely exemplary and are in no way limiting. For oral preparations, the GPR30 ligand can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The GPR30 ligand can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The GPR30 ligand can be utilized in aerosol formulation to be administered via inhalation. The compounds of the present invention can be formulated into pressurized acceptable propellants such as dichlorodifluoromethane, propane, nitrogen and the like.

Furthermore, the GPR30 ligand can be made into suppositories by mixing with a variety of bases such as emulsifying bases or water-soluble bases. The GPR30 ligand of the present invention can be administered rectally via a suppository. The suppository can include vehicles such as cocoa butter, carbowaxes and polyethylene glycols, which melt at body temperature, yet are solidified at room temperature.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing GPR30 ligand is placed in proximity to the site of action, so that the local concentration of active agent is increased relative to the rest of the body.

Unit dosage forms for oral or rectal administration such as syrups, elixirs, and suspensions may be provided wherein each dosage unit, for example, teaspoonful, tablespoonful, gel capsule, tablet or suppository, contains a predetermined amount of the compositions of the present invention. Similarly, unit dosage forms for injection or intravenous administration may comprise the compound of the present invention in a composition as a solution in sterile water, normal saline or another pharmaceutically acceptable carrier. The specifications for the novel unit dosage forms of the present invention depend on the particular compound employed and the effect to be achieved, and the pharmacodynamics associated with each active agent in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Methods of Use

A therapeutic dose of a GPR30 ligand is administered to a host suffering from a neurologic disorder. Administration may be topical, localized or systemic, depending on the specific disease. The compounds are administered at an effective dosage that over a suitable period of time substantially arrests the disease progression. It is contemplated that the composition will be obtained and used under the guidance of a physician for in vivo use.

The dose will vary depending on the specific GPR30 ligand utilized, type of disorder, patient status, etc., at a dose sufficient to substantially protect the neural cells from damage, dysfunction or death, while minimizing side effects. Treatment may be for short periods of time, e.g. after trauma, or for extended periods of time, e.g. in the prevention or treatment of Alzheimer's disease.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the array" includes reference to one or more arrays and equivalents thereof known to those skilled in the art, and so forth. All technical and scientific terms used herein have the same meaning as commonly understood to one of ordinary skill in the art to which this invention belongs unless clearly indicated otherwise.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Experimental

The reagents used in these studies were those specified in the original references to methods employed, unless otherwise specified. We used established cell culture methods for growing cells and for examining their morphological responses (Zhou et al. (1994) *Proc. Natl. Acad. Sci USA* 91(9):3824–3828). To examine gene expression for GPR30 and the classical ERs, standard methods were used to isolate mRNA and to analyze it by Northern blot and by RT-PCR (GIBCO-BRL, Bethesda, Md.). The activity of Rap1 and of Ras were assayed using pull-down assays with fusion proteins that bind specifically to the GTP-bound forms of these proteins, as described (Herrmann et al. (1995) *J. Biol. Chem.* 270:2901–2905). These fusion proteins were produced essentially as described by these authors. The activity of MAP kinase was determined by immunoblotting cell lysates with antibodies to phosphorylated MAP kinase (Payne et al. (1991) *EMBO J.* 10(4):885–892). The source of these antibodies was from New England Biolabs, Inc. (Beverley, Mass.).

The goal of these experiments was to ask if estrogen would activate GPR30 and induce the activation of signaling pathways known to be important for the survival and function of neurons. In short, to test the idea that estrogen acted through GPR30 to act as a neurotrophic and neuroprotective factor.

NGF is a polypeptide neurotrophic factor that acts to enhance the function and survival of certain neurons in both the central and peripheral nervous system (Yuen and Mobley (1996) *Ann Neurol.* 40(3):346–354). The ability of NGF to cause the differentiation of neuronal cells and to increase their functional status depends on its ability to induce persistent increases in the activity of MAP kinase and the signaling pathways in which it participates (Marshall (1995) *Cell* 80:179–185). We and others (York et al. (1998) *Nature* 392:622–626) have shown that NGF's ability to persistently activate MAP kinase is due to its ability to persistently activate an the small GTPase, called Rap1, that is upstream from MAP kinase. Using PC12 cells, neuron-like cells that have been used to model the signaling pathways activated by NGF and other neurotrophic factors, we asked whether estrogen would also activate Rap1.

Figure 1:
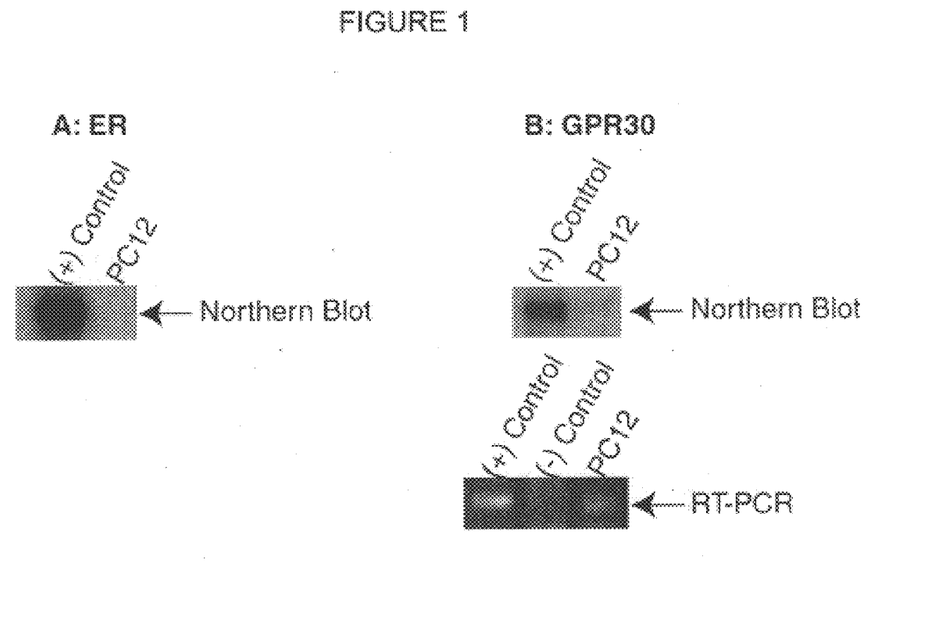
FIGS. 1A and 1B: Total poly(A)-mRNAs were extracted from PC12 cells, an ER- and GPR30-positive control cell line (+) and a GPR30-negative cell line (−). The mRNAs were separated, transferred and blotted with $^{32}$P-labeled probes specific for ERs (A) and GPR30 (B). The Northern blots show that, PC12 cells express no detectable ERs but a low level of GPR30 message. Expression of GPR30 in PC12 cells is further confirmed by RT-PCR using GPR30 specific primers. The results are presented in the lower panel of B.

The first goal of these studies was to determine whether or not GPR30 is expressed in PC12 cells. Using Northern blot and RT-PCR analyses, we found that it was expressed (FIG. 1). In recent experiments, Western blotting has shown that GPR30 protein is also present. Interestingly, GPR30 appears be the only estrogen receptor expressed in PC12 cells. Using the same methods, we did not detect the classical ERs in these cells.

Figure 2:
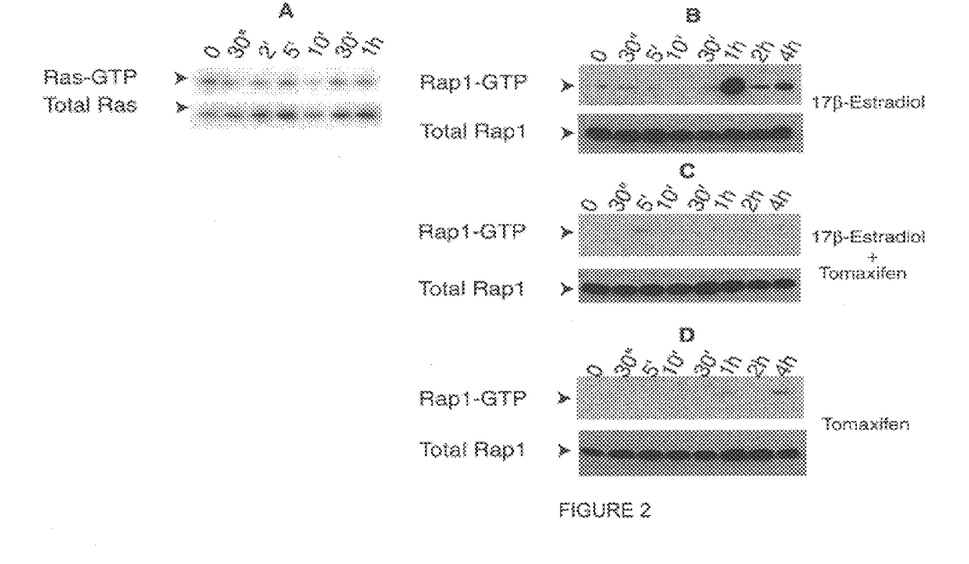
FIG. 2A, 2B, 2C, 2D: 17β-estradiol elicits Rap1, but not Ras, activation in PC12 cells. Serum-starved PC12 cells were treated with 100 nM 17β-estradiol for the indicated time intervals. Activated Ras (A) and Rap1 (B) were precipitated from cell lysates and analyzed as described in the Materials and Methods. The results show that 17β-estradiol induces Rap1 activation (B) and causes no detectable Ras activation (A). Rap1 activation induced by 100 nM 17β-estradiol can be blocked by 1 μM tomaxifen (C). Tomaxifen itself has no effect on Rap1 activation in PC12 cells (D).
Figure 3:
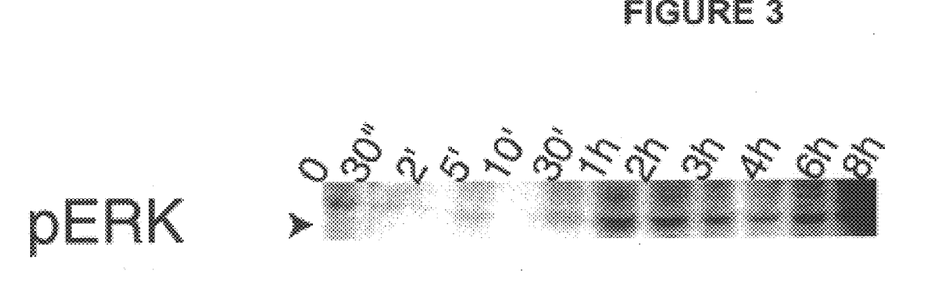
FIG. 3: 17β-estradiol induces prolonged Erk activation in PC12 cells. As in FIG. 2, serum-starved PC12 cells were treated with 100 nM 17β-estraldiol for the indicated time intervals. Cells were rinsed and lysed in RIPA buffer. Proteins were separated on SDS-PAGE, blotted onto PVDF membrane. The blot was probed for activated Erks (i.e activated MAP kinase) using rabbit IgGs against activated Erk kinases (UBI).

Once the expression of GPR30 in PC12 cells was confirmed, we set out to examine estrogen effects on Rap1 signaling. We found that 17β-estradiol activated Rap1, but not Ras (FIG. 2 A and B). Remarkably, it did so with a temporal pattern quite similar to what is seen with NGF. Like NGF, 17β-estradiol had little effect on the activation of Rap1 during the first 10 minutes of treatment and had a marked effect at later times. While tamoxifen, an estrogen antagonist, alone had no effect on Rap1 activity, it blocked the response to 17β-estradiol (FIG. 2 C and D). This suggests that the ligand binding site in GPR30 for 17β-estradiol accepts tamoxifen but is not activated by it. Importantly, like NGF, 17β-estradiol induced sustained activation of MAP kinase (FIG. 3). Indeed, the pattern for activation of MAP kinase (labelled as pERK in the Figure) closely paralleled that for activation of Rap1, a finding that is also seen with NGF.

Figure 4:
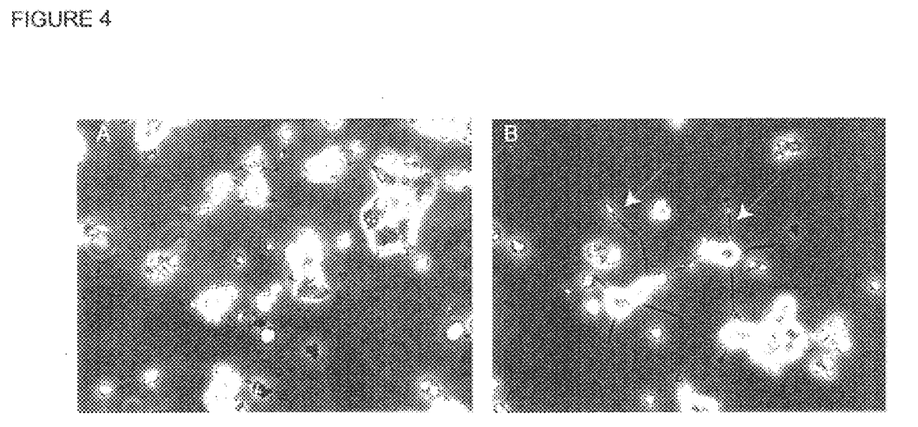
FIGS. 4A and 4B: 17β-estradiol induces PC12 cell differentiation. PC12 cells were maintained in either serum-free media (A) or serum-free media supplemented with 100 nM 17β-estradiol (B) for 6 days. Cells were monitored with phase-contrast microscope and typical images were captured using a CCD camera. Differentiated PC12 cells (arrows) can be observed with 17β-estradiol treatment (B), whereas massive cell death occurred in the control (A).
Figure 5:
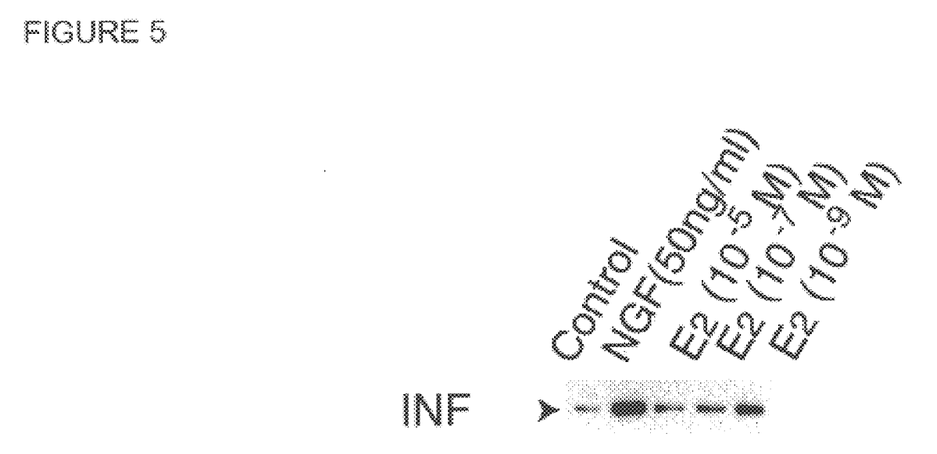
FIG. 5: Induction of the 145 kDa intermediate neurofilament expression by 17β-estradiol in PC12 cells. PC12 cells were maintained in either serum-free media supplemented with either NGF or 17β-estradiol at the indicated concentrations for 3 days. Treated as well as control cells were lysed in RIPA buffer and the lysates were separated on SDS-PAGE, transferred onto PVDF membrane. The blot was probed with specific antibodies against the 145 kDa intermediate neurofilament.

To ask if the signaling events induced by 17β-estradiol through GPR30 were reflected in changes in the structure and function of neurons, we tested the effects of 17β-estradiol on neuronal differentiation and survival. We discovered that 17β-estradiol induced the outgrowth of long neurites from PC12 cells (FIG. 4). This effect mirrors the actions of NGF. Like NGF, 17β-estradiol prevented these cells from dying under serum free culture, a condition well known to cause their death. Consistent with these findings, 17β-estradiol increased the differentiated state of PC12 cells by increasing the level of expression of the 145kDa intermediate neurofilament protein (FIG. 5). These observations show that 17β-estradiol acts as a neurotrophic factor for PC12 cells that express GPR30 in the absence of other estrogen receptors. They raise the possibility that estrogen signaling through GPR30 has potent effects on the viability and function of neurons, including those whose survival is threatened.

Our observations provide strong support for the view that GPR30 mediates the neurotrophic actions of estrogen in neuronal cells. The focus on GPR30 as a neurotrophic receptor will potentially lead to important new insights into estrogen signaling. This receptor is an important target of future drug discovery efforts aimed at preventing and treating neurodegenerative disorders.

What is claimed is:

1. A method of screening for neuroprotective agents, the method comprising:

combining a candidate agent with GPR30;

determining activation of GPR30 by said candidate agent;

combining said candidate agent with ESR1 or ESR2, determining activation of ESR1 or ESR2 by said candidate agent; wherein neuroprotective agents activate GPR30 but lack activation of ESR1 or ESR2.

2. The method of claim 1, wherein said activation of GPR30 is determined by an assay for activation of Rap1 or for activation of proteins involved in transmitting a signal from GPR30 to Rap1 or from RAP1 to the cell.

3. The method of claim 1, wherein said candidate is an estrogen derivative.

4. The method of claim 1, wherein said candidate agent is a derivative of a non-steroidal estrogen.

* * * * *

UNITED STATES PATENT AND TRADEMARK OFFICE
CERTIFICATE OF CORRECTION

PATENT NO.     : 6,265,147 B1
DATED          : July 24, 2001
INVENTOR(S)    : Mobley, William C. et al.

It is certified that error appears in the above-identified patent and that said Letters Patent is hereby corrected as shown below:

Column 7,
Line 9, please correct as follows:
-- Described by Green et al. (1986) *Nature* 320:134-139, --

Column 14,
Line 11, please correct as follows:
-- 3.  The method of claim 1, wherein said candidate agent is an --

Signed and Sealed this

Twenty-first Day of January, 2003

JAMES E. ROGAN
*Director of the United States Patent and Trademark Office*